United States Patent [19]

Church

[11] 4,218,538
[45] Aug. 19, 1980

[54] TWO STAGED CONTINUOUS FERMENTATION PROCESS FOR PRODUCTION OF HETEROPOLYSACCHARIDE

[75] Inventor: Brooks D. Church, Littleton, Colo.

[73] Assignee: Inpro, Inc., Rock Island, Ill.

[21] Appl. No.: 858,204

[22] Filed: Dec. 7, 1977

[51] Int. Cl.² .................. C12Q 19/04; C12M 1/40; C12R 1/64
[52] U.S. Cl. .................. 435/101; 435/288; 435/311; 435/313; 435/803; 435/813; 435/819; 435/910
[58] Field of Search ............... 195/31 P, 96, 115, 139; 210/23 F, 21 C; 435/101, 813, 910, 288, 311, 313, 819, 813, 803

[56] References Cited

U.S. PATENT DOCUMENTS

| | | | |
|---|---|---|---|
| 3,427,226 | 2/1969 | McNeely | 195/31 P |
| 3,472,765 | 10/1969 | Budd et al. | 210/23 F X |
| 3,485,719 | 12/1969 | Rogouin | 195/31 P |
| 3,647,632 | 3/1972 | Johnson et al. | 195/142 |
| 3,915,802 | 10/1975 | Kominek | 195/115 X |
| 4,130,461 | 12/1978 | Righelato et al. | 195/31 P |

OTHER PUBLICATIONS

Moraine et al., "Kinetics of Xanthan Fermentation", Chem. Abstracts, vol. 78 No. 21, p. 243, Abs. No. 134486 (1973).

Primary Examiner—Thomas G. Wiseman

[57] ABSTRACT

A continuous two-stage process for the production of heteropolysaccharide by Xanthomonas bacteria on selected cereal grain carbohydrate substrates. The growth phase and the cell population of the bacteria are totally separated from the polymerization of the biopolymer product.

6 Claims, 1 Drawing Figure

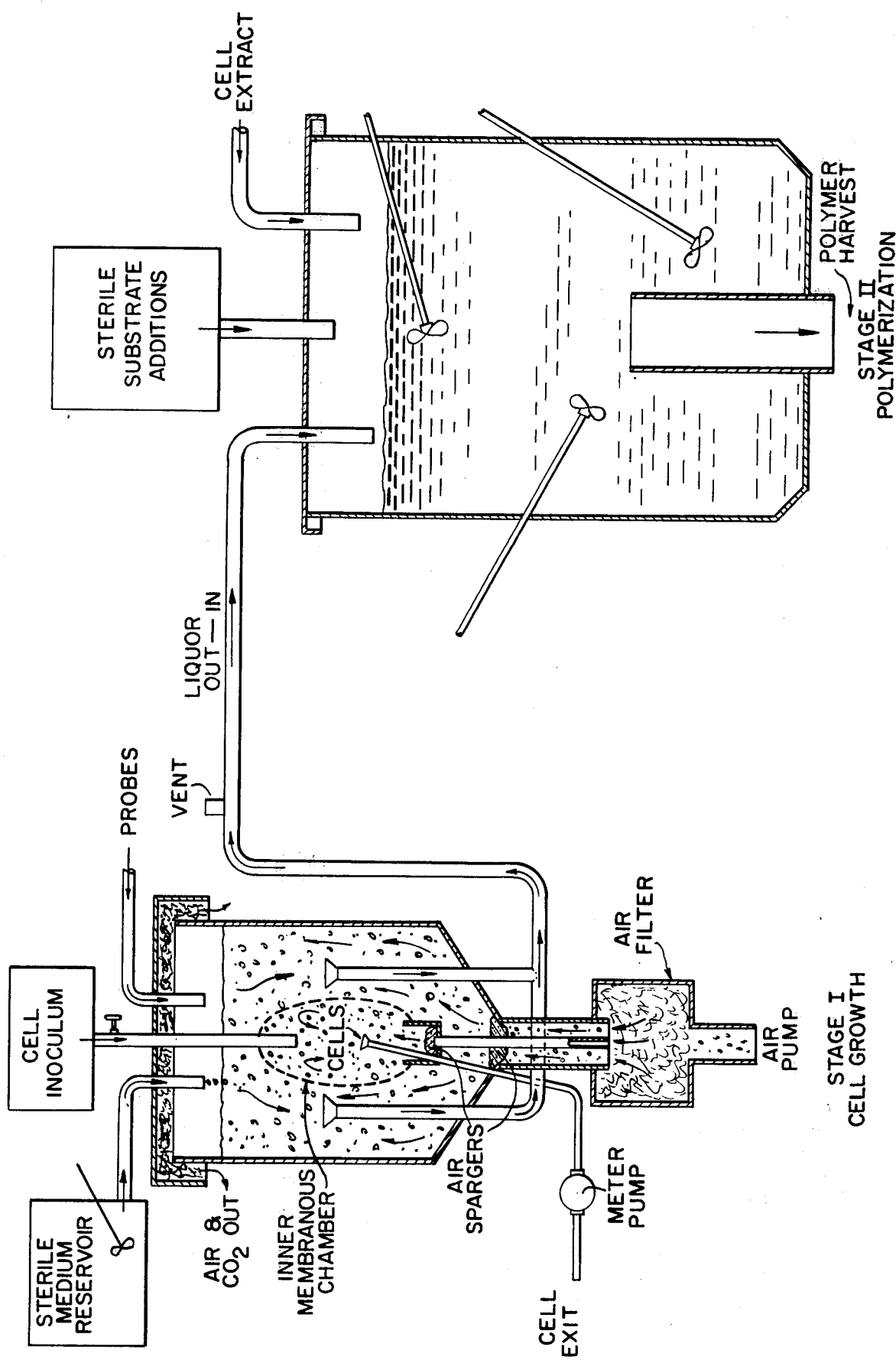

TWO STAGED CONTINUOUS FERMENTATION PROCESS FOR PRODUCTION OF HETEROPOLYSACCHARIDE

BACKGROUND OF THE INVENTION

The present invention relates to a continuous fermentation process for producing a heteropolysaccharide. Considerable interest in heteropolysaccharides produced by the bacterial fermentation of carbohydrates has been exhibited in recent years. Impetus has been given to the development of this interest by the discovery that certain heteropolysaccharides formed by biochemical synthesis have properties which permit their use as thickening agents for water used in secondary recovery operations carried out in the petroleum industry. It has been found that some of these materials added to water or brine in suitable concentrations produce viscous solutions which are relatively stable under the conditions which prevail in subsurface oil reservoirs. By utilizing a solution of controlled viscosity in place of or in addition to the water or brine normally employed in waterflooding projects, a favorable mobility ratio between the oil in the reservoir and the liquid used to displace it can be obtained. The tendency of the displacing medium to finger through highly permeable sections of the reservoir without displacing oil from the less permeable sections is greatly decreased. Viscous forces which normally reduce the displacement efficiency in portions of the reservoir through which the displacing medium actually passes are more readily overcome. As a result of these effects, the use of water or brine containing polysaccharide thickening agents generally permits the recovery of significantly greater quantities of oil during waterflooding than can be removed with water or brine alone.

A particularly effecting polysaccharide for use as a thickening agent during oil field waterflooding operations is the heteropolysaccharide produced by the action of bacteria of the genus Xanthomonas upon sugar, starches and similar carbohydrates. This material is more commonly known as "Xanthan gum". Studies and comparative tests have shown that this material, a polymer containing mannose, glucose, glucuronic acid salts, and acetyl radicals in a molar ratio of about 2:1:1:1 respectively, has much greater thickening power than dextran and similar polysaccharides and hence can be used in significantly lower concentrations than the other materials. It is effective in both fresh water and brine and has excellent high temperature stability characteristics. It is not precipitated or adsorbed to a significant extent upon contact with porous rock and sands commonly found in oil-bearing reservoirs. It exhibits little or no tendency to plug unconsolidatd sand reservoirs operations. The combination of all of these properties makes the heteropolymer formed by Xanthomonas organisms from carbohydrates considerably more attractive than other polysaccharides for use as water thickeners in secondary or tertiary recovery operations.

Although Xanthan gum has several uses in industrial application, primarily as a thickener in food processing and as a drilling "mud" in the oil industry, a new use has been developed in tertiary flooding of oil wells.

The best thickener known for use in tertiary flooding of oil wells is Xanthan gum, because it does not shear, clog the strata, or react with minerals underground. Xanthan gum has become the standard by which alternative compounds for this use are rated.

The heteropolysaccharide described above is normally produced by inoculating a medium containing from about 1 to about 5 percent by weight of a suitable carbohyrdrate, organic nitrogen sources, dipotassium hydrogen phosphate and appropriate trace elements with an organism of the genus Xanthomonas and then permitting the culture to incubate at about room temperature and under aerobic conditions for a period of about three to four days. Carbohydrates which may be employed in this manner include glucose, fructose, maltose, sucrose, lactose, galactose, soluble starch, e.g. corn starch and the like. Specific Xanthomonas organisms which may be used to produce heteropolysaccharides include *Xanthomonas campestris, Xanthomonas phaseoli, Xanthomonas malvacearum, Xanthomonas translucens, Xanthomonas carotae, Xanthomonas hederaz, Xanthomonas papavericola, Xanthomonas begoniae, Xanthomonas incanae, Xanthomonas vasculorum* and *Xanthomonas vesicatoria.* At the end of the incubation period, the crude polymer formed in the culture medium can be separated from the bacterial cells by centrifugation or filtration and can thereafter be isolated and purified by precipitating it with methanol, ethanol, acetone or a similar reagent. After drying, the heteropolymer is recovered as a light fluffy powder which may be slightly tinted by colored materials from the culture medium.

Conventional processes for making Xanthan gums involve either batch or continuous one or more stage processes. Although the conventional processes involve low capital cost, the cost of removal of cells in the product is high. Because the viscosity of the final product is high, the final product must be diluted to facilitate cell removal. Removal of the final product is generally effected by centrifugation or precipitation. During fermentation, the high viscosity of the polymer may prevent nutrients from getting to the cells, and therefore inhibit continued product formation. The yield of product, in dry weight, is based on the amount of original carbohydrate consumed. Total production time according to these processes is about 96 hours.

For many uses, a heteropolysaccharide of high salt, heat, and acid resistance is evaluated primarily on the basis of its viscosity characteristics. Since these viscosity characteristics are approximately the same for a crude product as for a refined product, where the same actual polymer concentration exists, it is economically feasible to produce a crude product. The term "crude" for this product is defined as a low-cost, bacteria-free, slightly off-white heteropolysaccharide polymer.

SUMMARY OF THE INVENTION

A new fermentation process has now been developed which will produce crude heteropolysaccharide in a sequential, two-stage, continuous facility. The continuous two-stage process of the present invention is unique in that the growth phase and the cell population of *Xanthomonas campastris* NRRL B1459 are totally separated from the polymerization of the bipolymer product.

The process according to the present invention is based on the discovery that the growth of the bacterial (Xanthomonas) population can be separated from the final phases of heteropolysaccharide synthesis. This phenomenon arises as a result of maintaining continuous cellular growth and metabolism in the late expotential--

-early stationary growth phases where only early steps of the heteropolysaccharide synthesis occur. The later or final heteropolysaccharide polymerization steps, in which the viscosity increases, can be conducted in the absence of the intact cellular components by virtue of extracellular enzymatic reactions effecting the condensation of cellularly excreted unit carbohydrate polymer intermediates.

The fermentation of the present invention has been designed to take advantage of these cellular metabolic activities by utilizing a sequential two-stage continuous process.

The process according to the present invention involves the separation of a continuous microbial growth of *Xanthomonas campestris* NRRL B1459 in the late expotential--early stationary growth phases (first stage) from the final polymerization phase of the viscous material (second stage). The second stage final polymerization phase is accomplished in a microbial cell-free system.

Both the microbial growth stage and the final polymerization stage are accomplished by using refined sugar or starches, food grade cereal grain milling products, or the waste products arising from the cereal milling processes.

Specifically, the first stage, or microbial growth phase, is conducted in a two-chambered fermentor. The inner chamber containing the microbial cell population is separated from the rest of the fermentor volume by a porous membrane bag. The outer chamber surrounding the membranous chamber of the fermentor contains the cell growth substrates. The porosity of the membranous chamber is such as to permit free mixing of the growth substrate-solubles between the chambers while disallowing migration of the bacterial cell population outside the membranous chamber.

Continuous operation of the dual chamber fermentation system of the first stage is carried out by allowing fresh sterile growth medium to flow into the outer chamber at a rate equal to the rate of removal of cells and growth medium from the two chambers. To produce the steady-state operation, the growth medium flow rate is adjusted to the specific growth rate of the bacterial population in the inner membranous chamber. Control of the steady-state is accomplished by utilizing the limiting concentration of the required nutrient dipotassium hydrogen phosphate.

The second stage or polymerization stage of the process is conducted in the absence of any intact cell. This is accomplished by allowing the exhausted liquor of the first stage to flow continuously into the second stage polymerizing facility. Since the polymerization time is two to three times longer than the growth doubling time of the cell population, the second stage facility is of necessity two to three times larger in volume than the facility for the first stage of the process. The second stage is two to three times larger in order to utilize the same flow-through rate which is determined to be optimal for steady-state operation of the first stage.

DETAILED DESCRIPTION OF THE INVENTION

The first stage of the process, according to the present invention, requires approximately six hours retention time. With longer times the capsular material (xanthan or heteropolysaccharide polymer) becomes so heavy as to inhibit free exocellular enzyme release into the surrounding medium. Next is the continuous polymerization with an approximate 20 hour turnover time of the second stage during which the cells in the first stage continuously produce minimum polymer and maximum enzymes. Growth rate, in the first stage, is controlled by adjusting the phosphate content of the fermentation medium and maintaining a near constant cellular level. With a continuous removal of medium and cells, a complete turnover of the system can be effected in approximately every twenty hours depending on the viscosity desired in the second state.

The dilution rate of the reaction is controlled by the flow rate of fresh medium into the reactor of specific volume at the same rate as the flow of spent medium and cells out of the reactor. The dilution rate is based on the specific growth rate of the cells in the late stage of growth. Exoenzymes and nutrients are freely exchanged through a membrane of 0.8 to 0.1$\mu$ porosity in the diameter of the minor bacterial cell axis. The bacterial cells have a size of approximately 1.0 to 3.0$\mu$.

In the first stage of the reaction, a 20% *Xanthamonas campestris* cell inoculum by volume of the membranous inner chamber is introduced. The medium for the *Xanthomonas campestris* cell growth is admitted and compromises the following:

| | % by weight in tap water |
|---|---|
| Dextrose | 0.80–1.0 |
| Corn steep liquor | 0.50–0.80 |
| Yeast extract | 0.10 (boiled aqueous) |
| $K_2HPO_4$ | 0.50 |
| $NH_4NO_3$ | 0.05 |
| $MgSO_4:7H_2O$ | 0.01 |
| Temperature 25°–28° C., pH 7.0 to 7.2 | |

Oxygen is introduced into the mixture of medium and cells at the rate of ⅔ volume of oxygen per volume of medium per minute. Aeration provides thorough mixing of the oxygen, nutrient, and cells throughout the first stage of growth system.

Ideally, the dextrose, nitrogen, and phosphate concentration in the medium during continuous operation should be near zero. If dextrose concentration is high (above 1%) polymer formation occurs during the first stage. The dextrose is used almost exclusively for cellular growth, and only a minimal amount is used for synthesis of early polymer intermediates. It has been found that the cell growth (numbers) is directly related to the concentration of dextrose in the reactor.

The dextrose concentration required to maintain a constant maximum cell number of between approximately 2.5 to 6.0×10 cells/ml. is 0.8 to 1.0 gm/100 ml. of medium. This data is shown in the Bi-Chamber Column of the following Table. It can also be seen, in the data shown here, that approximately 2 and 5 times more cells can be produced at 0.8 and 1.0% dextrose respectively than can be produced in the absence of the porous membrane. Although more cells can be produced at even higher dextrose levels (about 1% dextrose) than can be produced in the absence of the membrane, viscous polymer accumulation results in clogging of the membrane at these higher dextrose levels.

| Effect of Dextrose Concentration and Porous Membrane on Production of Cells | | |
|---|---|---|
| Dextrose Concentration % of Medium | Single Chamber Conventional Batch × $10^8$ cells/ml. | Bi-Chamber Membrane First Stage × $10^8$ cells/ml. |
| 0.2 | 8 | 9 |
| 0.4 | 30 | 26 |
| 0.6 | 86 | 90 |
| 0.8 | 120 | 248 |
| 1.0 | 119 | 640 |
| 1.2 | 122 | 1850 |
| 1.4 | 105 | 2610 |

Pure culture conditions are maintained in the first stage of the process. Sterile medium is fed to the first stage in which all medium components are pretreated by steam at 121° C. and 15 psi for 15 minutes, except the dextrose. 20% dextrose is separately sterilized under the same conditions as above or by filtration and then added in the appropriate concentration aseptically to the medium before medium admission to the first stage of the fermentor.

Aseptic conditions are not required in the second (polymerization) stage of the process. Scrupulous sanitation conditions, however, are employed and the second stage vessel is closed to the atmosphere. No contamination was detected in 8 of 10 experimental runs. Of the two experiments where contamination was detected, there were only 3 and 7 bacteria per 100 ml. respectively. Presumably, aseptic conditions prevail in the second stage because of the absence of inorganic nitrogen in the first stage effluent and in the nutrient additions entering the second stage reactor. Also, the increasing viscosity of the second stage reactor contents also precludes contaminant development.

The data showing the near absence of microorganisms in the second stage of this process is shown in the following table:

| Bacterial Contaminants in Seconds Stages of the Polymer Process | | | |
|---|---|---|---|
| Experiment Number | Days of Operation | 1st Stage Effluent Contaminants/100 ml. | 2nd Stage Medium Cotaminants/100 ml. |
| 1 | 4 | 0 | 0 |
| 2 | 10 | 0 | 0 |
| 3 | 5 | 1 | 0 |
| 4 | 7 | 0 | 7 |
| 5 | 6 | 0 | 0 |
| 7 | 14 | 0 | 0 |
| 8 | 20 | 0 | 0 |

By maintaining growth of the Xanthomonas cells continuously in the late expotential--early stationary phase and at a growth rate of $\mu = 0.116$ hr.$^{-1}$ which is a cell doubling time of 6 hours, reversion or selection of non-polymer producing variants were not observed during the time course of eight experiments.

Employing a laboratory-scale process in which the fist stage of the system contained a total volume of 9 liters (the inner membranous chamber containing the Xanthomonas cells constituted 3 liters of the first stage volume), a fresh sterile medium flow rate of 25 ml./min., and a second polymerization stage of 30 liters; consistent viscosity of approximately 10,000 c.p. was produced continuously, after the first 20 hours, at a rate of 1.5 liters/hr. for a period of 20 days. Seven other experimental runs also produced the same continuous viscosity when operated under these same conditions of time, temperature, pH and flow rate-although for overall shorter periods of time (less than 20 days) before termination of each experiment.

Periodic microscopic examinations of the Xanthomonas bacteria contained in the first stage inner membranous chamber revealed single cells of approximately 1 to $3\mu$ in size, non-motile, gram negative, with little or no capsular material. Samples of cellular material were streaked directly onto Difco YM Agar medium plates. The resultant colonies, after 24 to 36 hours incubation at 28° C., were large, yellow, and mucoid. Only rarely was a small, white, non-mucoid colony (indicitative of the non-polymer variant) observed. From such findings i.e., cell and colony morphology and no decrease in viscosity after 20 days of continuous operation, it was concluded that this system was unfavorable to the establishment of the non-polymer variant.

The second stage requires approximately twenty hours for completion. Therefore, the entire procedure requires approximately 20-30 hours, depending on how viscous a material is desired. For example, the relationship of time spent in the second stage to viscosity of the final product is as follows:

| Time in Second Stage | *Viscosity of Final Product |
|---|---|
| 17 hours | 6,000 cp |
| 24 hours | 12,000 cp |
| 30 hours | 18-20,000 cp |

*Viscosity measured at 5 rpm in a Brookfield Model HAT Viscometer

Control of the polymer reaction volume of the tank in which the second stage takes place defines the number of hours the material in the tank will have to polymerize since the reaction materials (enzymes and substrates) are flowing into the rank at a preset constant flow rate.

Enzyme containing (non-cellular) material from the first stage is introduced into the second stage tank for enzymatic polymer synthesis. In addition, 2% sugar (dextrose) is added. It may also be necessary to add a small amount of acid or base for pH control. The medium in the second tank comprises the following:

| | % by weight in tap water |
|---|---|
| Dextrose | 2.00–5.00 |
| $K_2HPO_4$ | 0.05 |
| $MgSO_4 \cdot 7H_2O$ | 0.01 |
| Yeast extract | 0.01 |
| KCl | 8.30 |

The reaction is conducted at 28° C., at pH ranging from 6.2 to 6.8. The 2 to 5% dextrose or starch may be refined, commercial grade or that contained in industrial processed cereal grain food fractions or wastes arising therefrom. Other sugars and starches e.g. sucrose, fructose, lactose, and modified industrial grade starches can also be polymerized. 65 to 70%, sometimes more, of the original carbohydrate added to the second state was converted to the biopolymer.

PROPERTIES OF THE GUM

Several properties of the gum produced by this process are summarized below:

1. Viscosity

The gum dissolves readily in hot or cold water to give high viscosity solutions at low concentration. A concentration of 1.5% gives a viscosity of approximately 20,000 cp when measured at 5 rpm on Model HAT Brookfield Viscometer.

2. pH Effect on Viscosity

Only small differences were observed in viscosity of the gum between the pH of 3 to 11.

3. Temperature Effect on Viscosity

The gum solution was examined to determine if any viscosity changes occurred at various temperatures between 30° C. to 120° C. It was found that the viscosity actually increases between 30° C. and 96° C. At 96° C. the gum showed a corresponding value of 120% of the original viscosity measured at 30° C. Above 96° C., the viscosity decreased markedly. All heating experiments were conducted for one hour at each temperature.

4. Salt Effect on Viscosity

The addition of NaCl enhanced the viscosity up to 20% salt. The salt concentrations did not insolubilize or precipitate the polymer from aqueous solution.

DETAILED DESCRIPTION OF THE DRAWINGS

The drawings illustrate a type of apparatus that can be used in the process according to the present invention.

In Stage I, the cell growth stage, the microbial growth is conducted in a bichamber fermentor. The inner chamber contains the microbial cell population. The inner chamber is separated from the rest of the fermentor volume by a porous membrane. The outer chamber surrounding the membranous inner chamber of the fermentor contains the cell growth substrates. The porosity of the membrane is such as to permit free exchange of the growth substrate solubles between the chambers while preventing migration of the bacterial cell population outside the inner chamber. Filtered air is introduced into the fermentor at the bottom to provide sufficient oxygen for the aerobic fermentation as well as to provide agitation of the medium and cells.

The first stage fermentor system is operated continuously by allowing fresh growth medium to flow into the outer chamber at a rate equal to the rate of removal of cells and growth medium from the two chambers. In the steady-state, the specific growth rate of the bacterial population in the inner chamber determines the flow rate of the growth medium per unit fermentor volume and thus the dilution rate of the whole process.

The polymerization stage, Stage II, is conducted in the absence of any intact cells and is virtually nitrogen free. This is accomplished by continuously introducing the spent growth medium of the first stage into the second stage polymerization facility. Since the polymerization time is two to three times longer than the growth doubling time of the cell population, the second stage facility is two to three times larger in volume than the first stage facility to provide for steady-state operation of the entire two stage process.

What is claimed is:

1. A two stage process for the production of a cell-free heteropolysaccharide polymer by the fermentation of a suitable carbohydrate with bacteria belonging to the Xanthomonas genus, wherein in the first stage, bacteria are continuously cultivated to produce exocellular polymerizing enzyme material and in the second stage, polysaccharide is produced in a cell-free system, comprising:

(a) continuously cultivating viable bacteria of the genus Xanthomanas characterized as being in the late exponential-early stationary growth phase in an inner membranous chamber of a fermentation vessel containing a carbohydrate fermentation media at a pH of 7.0 to 7.2 and at a temperature of about 28° C. under conditions suitable for maintaining the bacteria in the late exponential-early stationary growth phase and producing exocellular polyerizing enzyme material, (b) continuously separating and transfering said exocellular enzyme material from the fermentation media to a second vessel to form a cell-free fermentation media containing said exocellular enzyme material and substrate, (c) maintaining said cell-free fermentation media in said second vessel at a pH of 6.5 to 6.8 and at a temperature of about 28° C. to form heteropolysaccharide polymer, and (d) continuously withdrawing said polysaccharide polymer from the cell-free media.

2. A process according to claim 1 wherein a higher number of bacterial cells are produced compared to a non-membranous batch culture system and wherein a corresponding higher number of exocellular enzyme molecules are also produced.

3. A process according to claim 1 wherein an increased production of exocellular enzymes shortens the time of polymerization in the second or polymerization stage.

4. A process according to claim 1 wherein the polymer producing system is unfavorable for the establishment of non-polymer producing Xanthomonas variants.

5. A process according to claim 1 wherein the bacteria are *Xanthomonas campestris.*

6. A process according to claim 1 wherein the bacterial cells are separated from the enzyme containing medium to be transferred to the second stage vessel by a porous membrane.

* * * * *